United States Patent [19]

Sullivan

[11] Patent Number: 5,074,662

[45] Date of Patent: Dec. 24, 1991

[54] SAMPLE HOLDER FOR SPECTROSCOPIC STUDIES OF OPTICAL FILM

[75] Inventor: William Sullivan, Gillette, N.J.

[73] Assignee: Hoechst Celanese Corporation, Somerville, N.J.

[21] Appl. No.: 486,633

[22] Filed: Feb. 27, 1990

[51] Int. Cl.[5] .......................... G01N 21/01; B01L 9/00
[52] U.S. Cl. ...................................... 356/244; 422/104
[58] Field of Search .............. 356/244, 246, 300, 319, 356/326; 350/531; 422/104, 102

[56] References Cited

U.S. PATENT DOCUMENTS

| | | | |
|---|---|---|---|
| 2,637,817 | 5/1953 | Herbert | 356/246 |
| 3,527,542 | 9/1970 | Penhasi et al. | 356/244 |
| 3,895,873 | 7/1975 | Dennison et al. | 350/244 |
| 4,159,875 | 7/1979 | Hauser | 356/244 |
| 4,387,990 | 6/1983 | Yazawa et al. | 356/244 |
| 4,652,095 | 3/1987 | Mauro | 356/244 |
| 4,682,890 | 7/1987 | de Macaroo et al. | 356/244 |
| 4,934,817 | 6/1990 | Gassenhuber | 356/244 |
| 4,980,551 | 12/1990 | Wong | 350/244 |

Primary Examiner—Richard A. Rosenberger
Assistant Examiner—Hoa Pham
Attorney, Agent, or Firm—Lynch, Cox, Gilman & Mahan

[57] ABSTRACT

The invention disclosed is a sample holder support unit for holding an optical film sample securely and precisely within a spectroscopic device such as a spectrophotometer. The device of the instant invention is comprised of a base plate, connected thereto a back support and a removable sample holder which will slide over the back support to be held securely and accurately in place. The device permits the repositioning of an optical film sample repeatedly in the same place thus allowing for accurate and repetitive measurements of changes in the sample.

17 Claims, 7 Drawing Sheets

SAMPLE HOLDER FOR SPECTROSCOPIC STUDIES OF OPTICAL FILM

BACKGROUND OF INVENTION

1. Field of Invention

This invention concerns a holder of optical film components. In particular, this invention concerns a sample holder to precisely position optical films with an optical display unit for spectroscopic study.

2. Prior Art

A large variety of devices have been designed to position sample holders within various optical display units, such as spectrophotometers. For example, U.S. Pat. No. 4,652,095 discloses an optical component positioning device for the positioning of light optical components within an optical display unit. This device is comprised of a pair of plates having rail receiving grooves, a pair of rails joining the plates and a mounting table slidably disposed between the rails and the plates. While this device provides a means to move a microsample within an optical device, once the sample is positioned, it cannot be easily removed or repositioned for repeated viewing. Further, this device is quite complicated and its use is limited.

U.S. Pat. No. 4,682,890 discloses a microsample holder and carrier for use in a horizontal beam spectrophotometer. It is comprised of a carrier formed by a rectangular base and slotted arms for the receipt of a microsample holder. The microsample holder contains a series of openings for the receipt of microsamples. The device is designed to replace conventional cuvette supports, such as is shown in FIG. 1 of that patent. This device is limited in use as a replacement for cuvette holders. In addition, it does not permit the reexamination of a sample or for the measurement of changes in various light related activities, such as refractive index thickness by interference spectra. Without this ability to accurately reposition the sample, variations in film thickness may outweigh changes caused in the sample by other light sources.

U.S. Pat. No. 2,637,817 discloses a sealed variable length cell and positioner for use specifically with an infrared spectrometer. This device provides a sealed cell whose thickness can be adjusted depending upon the amount of liquid that is contained within the cell. This device clearly is not designed as a holder for use in a spectrophotometer.

None of these patents disclose an easy-to-use, simple device for holding optical film components in spectroscopic equipment.

Accordingly, it is an object of this invention to provide a device for holding an optical film in optical instruments.

It is a further object of this invention to provide a device for holding a sample holder which permits the accurate repositioning of the sample holder within an optical instrument.

It is a still further object of this invention to provide a device for holding a sample holder for use with a spectrophotometer.

It is a still further object of this invention to disclose a device for holding a sample holder to precisely position and reposition an optical film sample within a spectrophotometer.

These and other objects, as well as the scope, nature and utilization of the invention will be apparent from the following detailed description.

SUMMARY OF INVENTION

In accordance with the present invention there is provided a sample holder support unit for holding an optical film sample comprised of:
a) a base plate;
b) a back support secured to the base plate; and
c) a removable sample holder connectable to the back support, wherein said removable sample holder contains a back portion and a front portion, wherein said front portion contains a slot for holding the optical film sample and wherein there is a view opening running through the removable sample holder.

BRIEF DESCRIPTION OF THE DRAWINGS

The invention will now be described with reference to the accompanying drawings in which.

DETAILED DESCRIPTION OF PREFERRED EMBODIMENT

Spectrophotometers have long been used as a laboratory tool for analyzing or testing liquid samples of chemical solutions or mixtures, biological materials, biochemical materials, biochemical reactions and the like. In reviewing the effect of a light beam passing through a sample, it is frequently important to analyze repeatedly that same sample placed in the same position within the spectrophotometer to determine variations in the sample. The instant invention discloses a device which permits the accurate, repeated positioning of a sample in a spectrophotometer. For example, the instant invention is specifically designed for use in horizontal beam spectrophotometers such as a Lambda 9, U.V.-VIS/NIR spectrophotometer manufactured by Perkin-Elmer. The sample holder support unit of the instant invention provides a method to precisely and easily position a sample holder in the spectrophotometer to view it repeatedly and accurately.

Figure 1:
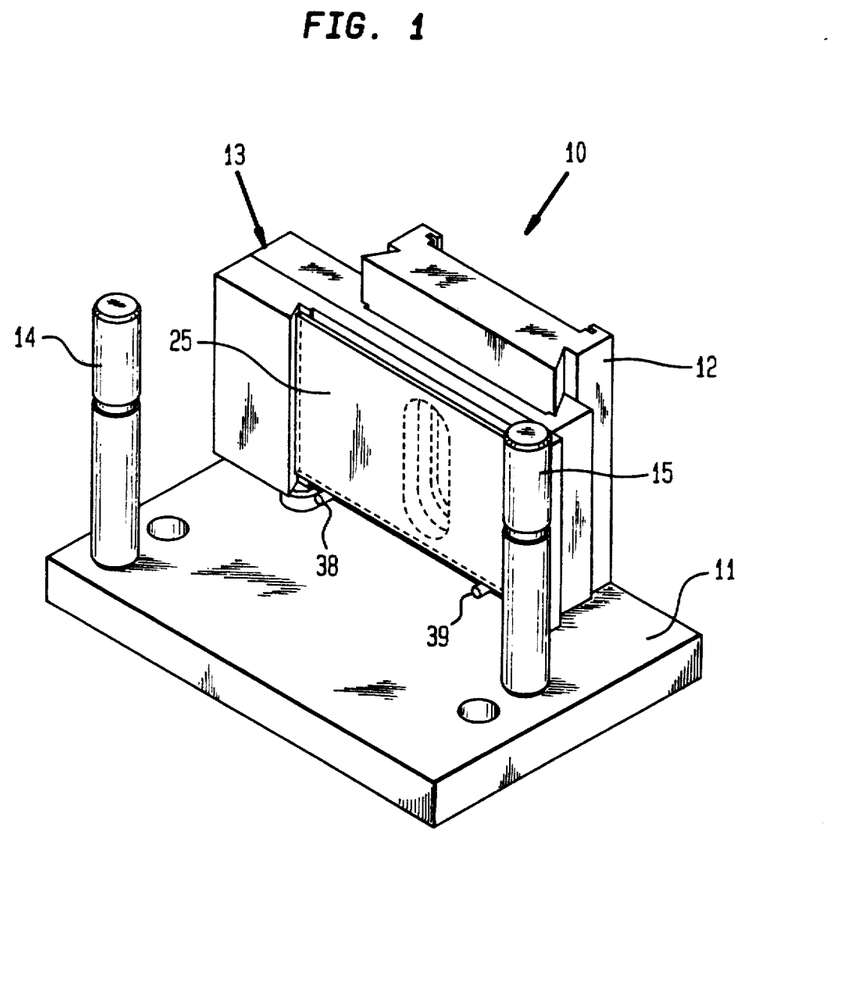
FIG. 1 is a front perspective view of the sample holder support unit.
Figure 2:
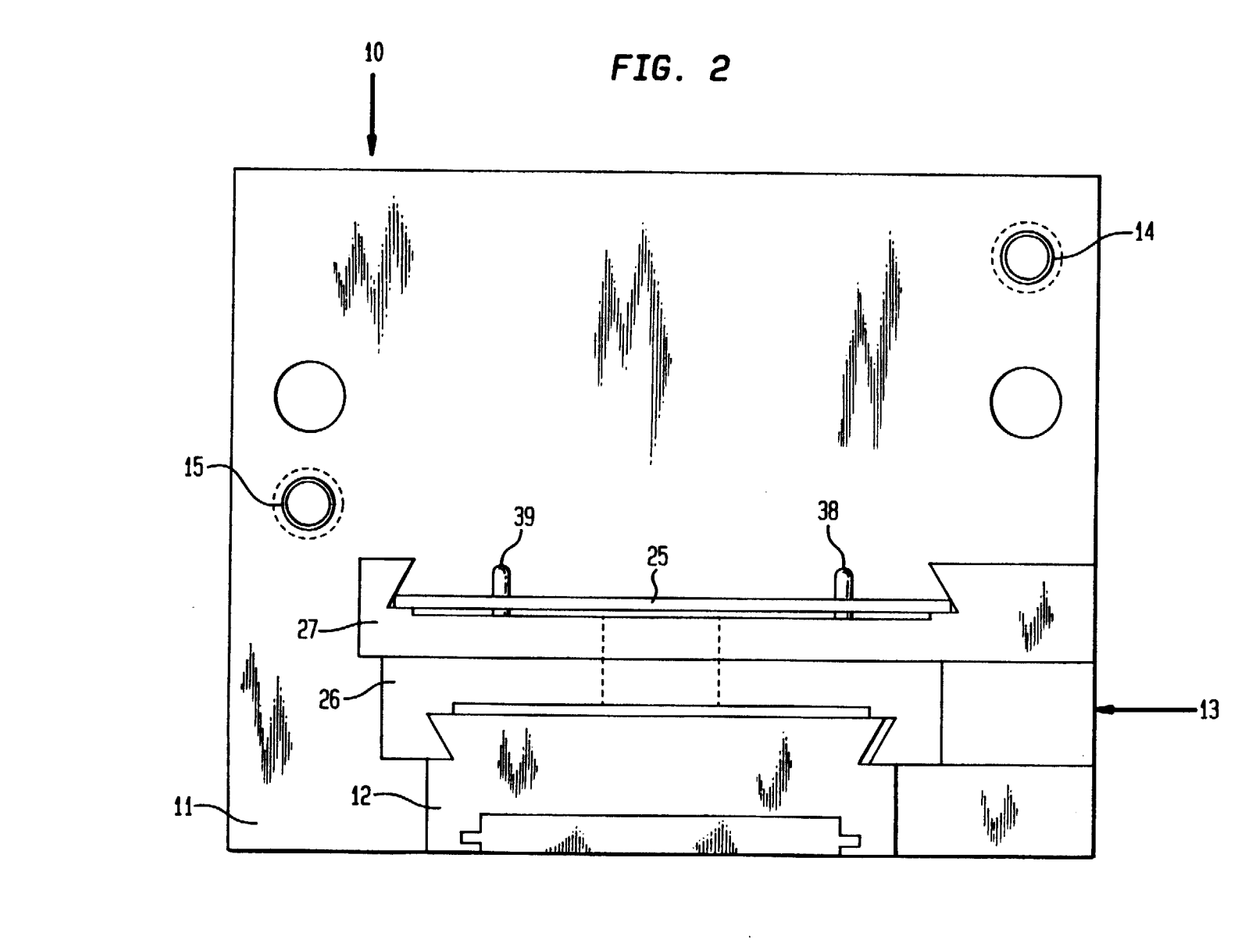
FIG. 2 is a top view of the sample holder support unit.

Although the invention is adaptable to a wide variety of uses, it is shown in the Figures for the purpose of illustration in a preferred embodiment as a sample holder support unit (10) comprised of a base plate (11), a back support (12) secured to the base plate and a removable sample holder (13) which is slidably connected to the back support. See FIGS. 1 and 2.

Figure 5:
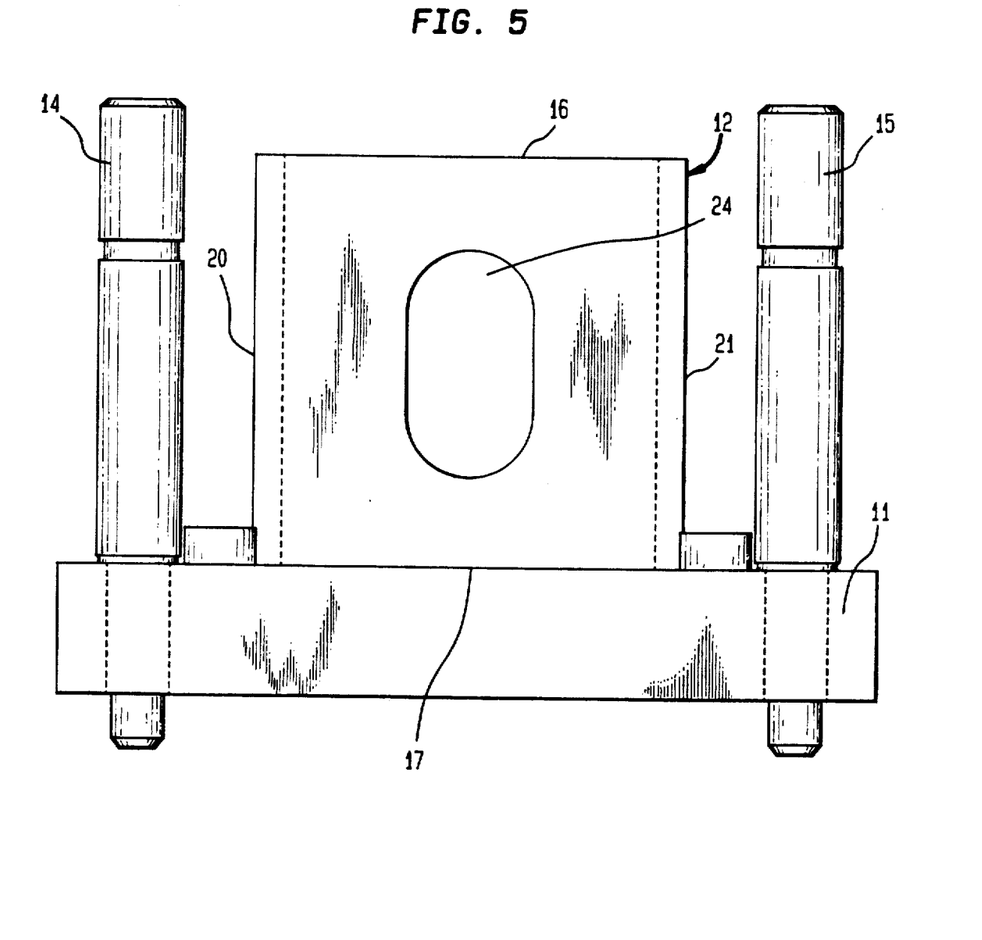
FIG. 5 is a back view of the base plate with attached back support.

The base plate (11) of the instant invention can be of any size or shape which will adequately support the other elements of the invention and which can be secured to the surface of a spectrophotometer. In a preferred embodiment, the base plate is generally rectangular in shape, approximately 3 to 6 inches in length and width, approximately ¼ to 1¼ inches in thickness, and manufactured from any conventional, sturdy material such as aluminum, brass, ceramic or the like. See FIGS. 2 and 3. The base plate is secured to the surface of a spectrophotometer by any conventional securing means. For example, screws or bolts running through the base plate can be secured to openings in the surface of the spectrophotometer. In a preferred embodiment for ease of use, a plurality of hand-adjustable, knurl-headed screws (14, 15) are used to secure the base plate to the surface of the spectrophotometer. See FIGS. 3 and 5.

Figure 4:
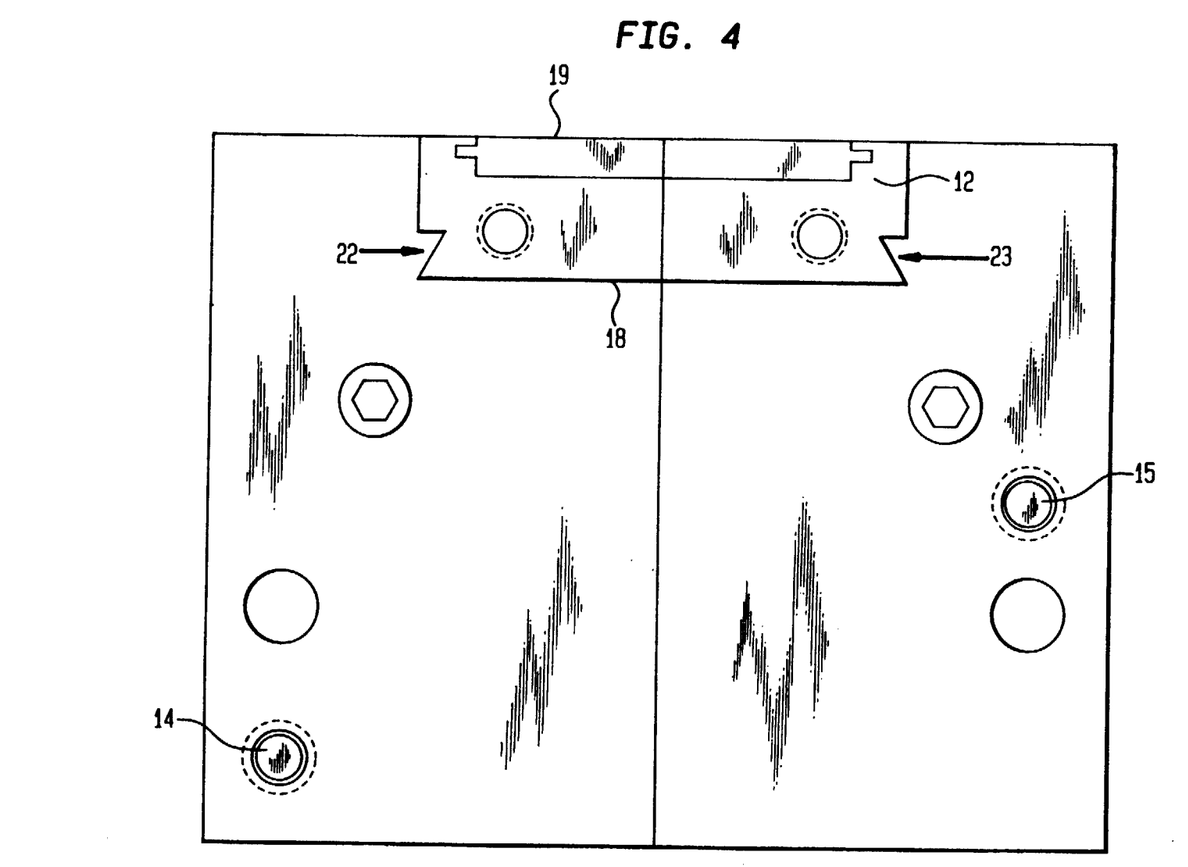
FIG. 4 is a top view of the base plate with attached back support.

Secured to the surface of the base plate (11) is the back support (12). In a preferred embodiment, the back support is secured against the top surface of the base plate generally near one of its edges. See FIGS. 4 and 5. The back support is secured to the base plate by any conventional securing means such as bolts, screws, welds and the like.

Figure 3:
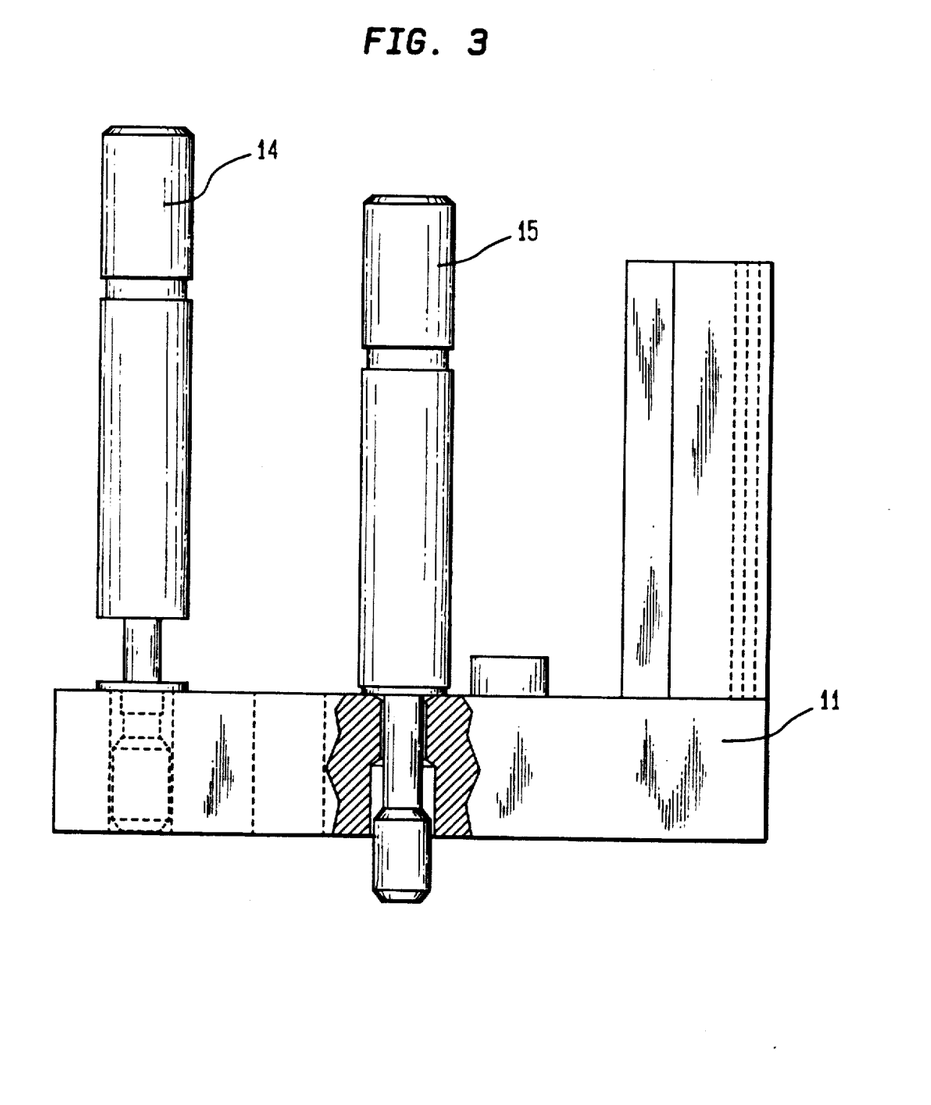
FIG. 3 is a side view of the sample holder support unit.

The back support (12) can be of any convenient size or shape as long as it fits on the base plate. In a preferred embodiment it is generally rectangular in shape, about 1 to about 6 inches in height and length and about ¼ to about 1 inch in thickness. See FIG. 4. It is generally manufactured from the same material as is the base plate. The back support has a top (16), bottom (17), front (18), back (19) and two sides (20, 21). Running down both sides the full height of the back support are a pair of back support grooves (22, 23). While these grooves can be of any shape or size, preferably they are V-shaped as shown in FIG. 3. In addition, there is provided a view opening (24) running through the back support which permits light to pass through the sample. See FIG. 5. This opening runs parallel to the surface of the base plate and can be of any size or shape sufficient to permit light to pass through the back support. In a preferred embodiment, the view opening is generally oval in shape.

Figure 6:
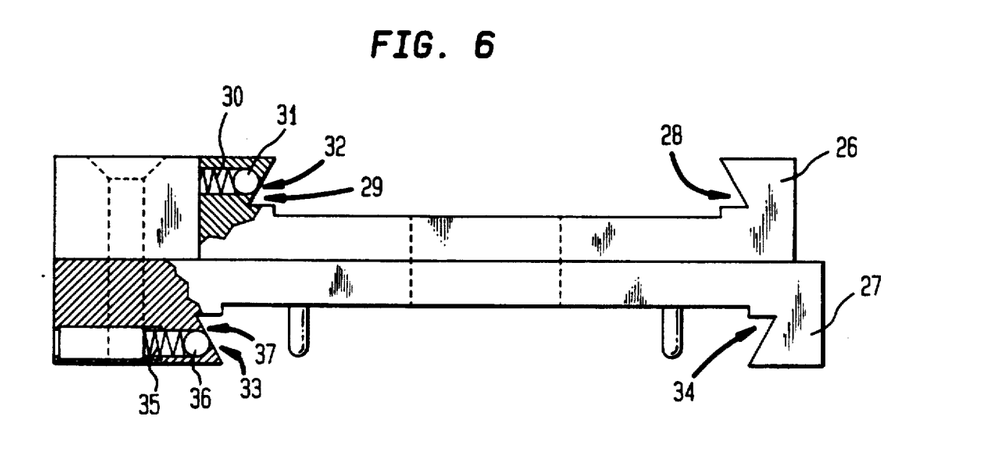
FIG. 6 is a top view of the removable sample holder.

The removable sample holder fits (13) onto the back support (12) to hold securely a sample (25) for viewing. The removable sample holder is comprised of a back piece (26) and a front piece (27) which are held together by any conventional securing means such as screws, bolts or by welds. See FIG. 6. The back piece of the removable sample holder contains a pair of back piece slots (28, 29) which interconnect with the back support grooves (22, 23) of the back support to permit the removable sample holder to slide onto and be held firmly in place by the back support. See FIG. 6. The removable sample holder back piece slots can be any size or shape, but preferably is V-shaped creating a mirror image of the back support grooves.

Contained in at least one side of the removable sample holder back piece slots is a back piece biasing means. In a preferred embodiment the back piece biasing means is comprised of a compressed coil spring (30) pressing upon a ball bearing (31) through a back piece biasing opening (32) in the side of one of the removable sample holder back piece slots (29) wherein this opening is less than the diameter of the ball bearing. See FIG. 6. The ball bearing is forced partially out of the back piece biasing opening by the pressure of the compressed coil spring. Since the ball bearing (31) is pressed by the coil spring (30), it will continually press against any device placed against that side of the back piece slot. This back piece biasing means is designed to hold the removable sample holder (13) safely, securely and consistently in the same position in the back support grooves (22, 23).

The front piece of the removable sample holder contains many of the same elements as are contained in the back piece of the removable sample holder. See FIG. 6. For example, the front piece contains a pair of front piece slots (33, 34) into which the sample holder (25) to be viewed is inserted. The sample holder front piece slots are designed to be slightly wider than is the sample holder to be viewed.

In at least one of the sides of the front piece slots of the removable sample holder is a front piece biasing means. See FIG. 6. In a preferred embodiment the front piece biasing means is of similar construction and shape to the back piece biasing means contained in the back piece and is comprised of a front piece compressed coil spring (35) pressing against a ball bearing (36) through a front piece biasing opening (37) in the side of one of the front piece slots. It performs the same function as does the back piece biasing means which is to hold securely, safely and consistently any device placed between the slots of the front piece of the removable sample holder. Specifically the back piece biasing means will hold the sample securely in place for viewing.

Figure 7:
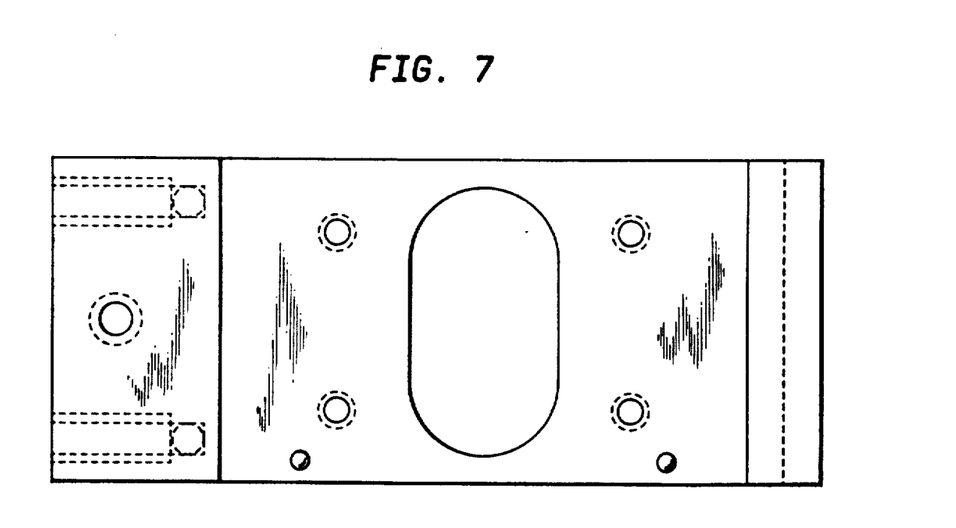
FIG. 7 is a front view of the removable sample holder.

To hold the sample holder at the correct height there is secured to the removable sample holder and projecting from the surface of the front piece within the area of the front piece sample holder opening, a pair of supporting pins (38, 39) which prevent the sample holder from being pushed too far down into the front piece slots of the removable sample holder. See FIGS. 6 and 7. These pins can be any conventional type as long as they project from the surface of the removable sample holder a sufficient distance to prevent the sample holder from dropping.

Figure 8:
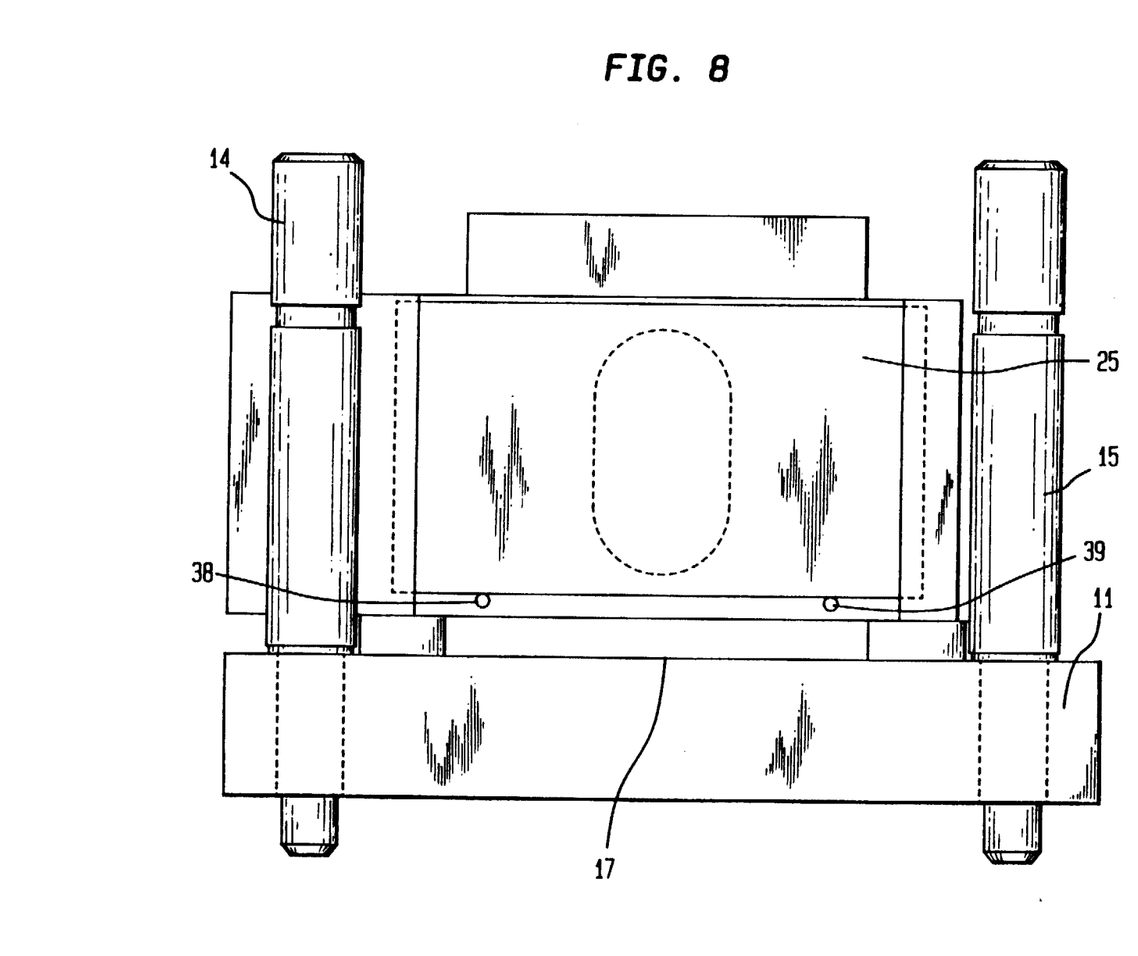
FIG. 8 is a back view of the sample holder support unit.

Running through both the front piece and the back piece of the removable sample holder is a removable sample holder view opening (40) whose size and shape are approximately the same as is the back piece opening. See FIGS. 7 and 8. The purpose of the removable sample holder view opening is the same as that of the back piece view opening (24), which is to permit light to pass through a sample holder held in the removable sample holder.

Different size removable sample holder can be produced with different openings which will hold different size sample holders. By varying the size of the front piece opening many sizes of sample holders can be held by the removable sample holder.

In operation, the base plate (11) with attached back support (12) of the sample holder support unit (10) is secured in the appropriate location within an optical instrument, such as a spectrophotometer. It is secured in place by screwing knurl-headed screws (14, 15) into predrilled holes in the surface of the spectrophotometer. The sample holder (25) for viewing is placed within the front piece slots (33, 34) of the removable sample holder (13). The sample holder (25) for viewing will be held in place by the action of the supporting pins (38, 39) at the bottom of the removable sample holder, the slots (33, 34) in the sides of the removable sample holder and the front piece coil spring biasing means which presses against the side of the sample holder (13). The removable sample holder is then secured in place by sliding the back piece (26) of the removable sample holder over the grooves (22, 23) in the back support. The removable sample holder is securely held in place by the interaction of the slots (28, 29) in the back piece of the removable sample holder and the grooves (22, 23) in the back support, and in addition, the back piece coil spring biasing means which acts against the sides of the slots of the back support. By this operation a sample holder (25) can be held securely and accurately in place and can be repositioned repeatedly for viewing through a optical device such as a spectrophotometer.

I claim:

1. A sample holder support unit for holding an optical film sample comprised of:
   a) a base plate;
   b) a back support secured to the base plate, said back support containing a back support groove and a back support view opening; and
   c) a removable sample holder connected to the back support, wherein said removable sample holder contains a back piece, said back piece containing a back piece slot adapted to slidably interconnect with the back support groove; a front piece having a slot for holding the optical film sample; and wherein there is a view opening running through the removable sample holder.

2. The sample holder support unit of claim 1 wherein there is contained within the back piece slot of the removable sample holder a back piece coil spring biasing means.

3. The sample holder support unit of claim 2 wherein the back piece coil spring biasing means is comprised of a coil spring pressing against a ball bearing projecting from the side of the back piece slot.

4. The sample holder support unit of claim 1 wherein the slot within the front piece of the removable sample holder contains at least one front piece biasing means.

5. The sample holder support unit of claim 4 wherein the front piece biasing means is comprised of a coil spring pressing against a ball bearing projected from the side of the front piece slot.

6. The sample holder support unit of claim 1 wherein the view opening passing through the back support and the view opening passing through the removable sample holder are oval.

7. The sample holder support unit of claim 1 wherein the base plate is produced from a material selected from the group consisting of aluminum, brass and ceramic material.

8. The sample holder support unit of claim 1 wherein projecting from the surface of the front piece is a pair of supporting pins.

9. A sample holder support unit for spectroscopic study of optical film samples comprising
   a) a base plate;
   b) a back support secured to the base plate wherein said back support contains a pair of back support grooves and a back support view opening; and
   c) a removable sample holder connected to the back support comprised of a back piece containing back piece slots wherein contained within the side of at least one of the back piece slots is a back piece coil spring biasing means, a front piece secured to the back piece containing front piece slots, wherein contained within at least one side of the front piece slots is a front piece biasing means, a pair of support pins projecting from the surface of the front piece, and a view opening passing through both the front piece and the back piece.

10. The sample holder support unit of claim 9 wherein the back piece biasing means is comprised of a coiled spring pressing against a ball bearing projecting from the side of one of the back piece slots.

11. The sample holder support unit of claim 9 wherein the front piece biasing means is comprised of a coiled spring pressing against a ball bearing projecting from the side of the front piece slot.

12. The sample holder support unit of claim 9 wherein the slots in the back support, back piece and front piece are V-shaped.

13. The sample holder support unit of claim 9 wherein the removable sample holder is connected to the base plate by the interaction of a slot contained in the back support with a slot contained in the back of the removable sample holder.

14. The sample holder support unit of claim 9 wherein the view opening passing through the back support and the view opening passing through the removable sample holder are oval.

15. The sample holder support unit of claim 9 wherein the base plate is produced from a material selected from the group consisting of aluminum, brass and ceramic material.

16. The sample holder support unit of claim 9 wherein projecting from the surface of the front piece is a pair of supporting pins.

17. The sample holder support unit of claim 9 wherein the means for securing the front piece to the back piece is by a screw posing through both pieces.

* * * * *